US009757737B2

(12) United States Patent
Katsumoto et al.

(10) Patent No.: US 9,757,737 B2
(45) Date of Patent: Sep. 12, 2017

(54) CELL SORTING APPARATUS, CELL SORTING CHIP AND CELL SORTING METHOD

(71) Applicant: Sony Corporation, Tokyo (JP)

(72) Inventors: Yoichi Katsumoto, Tokyo (JP); Kazumasa Sato, Tokyo (JP); Heloise Cockenpot, Paris (FR)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/881,340

(22) Filed: Oct. 13, 2015

(65) Prior Publication Data

US 2016/0030950 A1   Feb. 4, 2016

Related U.S. Application Data

(63) Continuation of application No. 13/279,033, filed on Oct. 21, 2011, now Pat. No. 9,164,023.

(30) Foreign Application Priority Data

Oct. 29, 2010   (JP) .................................. 2010-244096

(51) Int. Cl.
*B03C 5/00*   (2006.01)
*G01N 15/14*   (2006.01)
(Continued)

(52) U.S. Cl.
CPC ........ *B03C 5/005* (2013.01); *B01L 3/502761* (2013.01); *B03C 5/026* (2013.01);
(Continued)

(58) Field of Classification Search
CPC ....... B03C 5/00–5/028; B03C 2201/18; B03C 2201/16; B01L 3/502761; G01N 15/06
See application file for complete search history.

(56) References Cited

U.S. PATENT DOCUMENTS 5,489,506 A   2/1996 Crane
2007/0240495 A1   10/2007 Hirahara
(Continued)

FOREIGN PATENT DOCUMENTS

JP   2002-528699   9/2002
JP   2003-287519   10/2003
(Continued)

OTHER PUBLICATIONS

Chinese Office Action issued Jan. 20, 2014 for corresponding Chinese Appln. No. 201110324742.6.
Japanese Office Action issued Jan. 28, 2014 for corresponding Japanese Appln. No. 2010-244096.
(Continued)

*Primary Examiner* — J. Christopher Ball
(74) *Attorney, Agent, or Firm* — K&L Gates LLP

(57) ABSTRACT

A cell sorting apparatus includes a flow channel through which fluid including cells flows, an electric-field application section capable of applying an electric field having a gradient in a direction different from the flowing direction of the fluid at a first position on the flow channel in accordance with a cell sorting signal requesting an operation to sort the cells, and a flow splitting section configured to split the cells changing their flowing directions due to a dielectrophoretic force caused by application of the electric field at a second position on the downstream side of the first position on the flow channel.

20 Claims, 7 Drawing Sheets

(51) Int. Cl.
- *C12M 3/06* (2006.01)
- *C12M 1/00* (2006.01)
- *B01L 3/00* (2006.01)
- *B03C 5/02* (2006.01)
- *C12N 13/00* (2006.01)
- *G01N 15/10* (2006.01)

(52) U.S. Cl.
CPC ............ *C12M 23/16* (2013.01); *C12M 47/04* (2013.01); *C12N 13/00* (2013.01); *G01N 15/14* (2013.01); *G01N 15/1404* (2013.01); *G01N 15/1459* (2013.01); *G01N 15/1484* (2013.01); *B01L 2200/0652* (2013.01); *B01L 2300/0816* (2013.01); *B01L 2300/0864* (2013.01); *B01L 2400/0424* (2013.01); *G01N 2015/1006* (2013.01); *G01N 2015/149* (2013.01)

(56) References Cited

U.S. PATENT DOCUMENTS

| | | |
|---|---|---|
| 2008/0176211 A1 | 7/2008 | Spence et al. |
| 2009/0294291 A1 | 12/2009 | Voldman et al. |
| 2012/0103813 A1* | 5/2012 | Sato ...................... B03C 5/026 204/547 |

FOREIGN PATENT DOCUMENTS

| | | |
|---|---|---|
| JP | 2003-507739 | 10/2003 |
| JP | 2010-025911 | 2/2010 |
| JP | 2010-181399 | 8/2010 |
| JP | 2012-522518 | 9/2012 |
| WO | 2005/121767 | 12/2005 |

OTHER PUBLICATIONS

Japanese Office Action issued Sep. 9, 2014 for corresponding Japanese Appln. No. 2010-244096.

* cited by examiner

CELL SORTING APPARATUS, CELL SORTING CHIP AND CELL SORTING METHOD

CROSS REFERENCES TO RELATED APPLICATIONS

The present application is a continuation of U.S. application Ser. No. 13/279,033, filed Oct. 21, 2011, which claims priority to Japanese Priority Patent Application JP 2010-244096 filed in the Japan Patent Office on Oct. 29, 2010, the entire content of each of which is hereby incorporated by reference herein.

BACKGROUND

The present disclosure relates to a cell sorting apparatus for sorting target cells, a cell sorting chip implementing the apparatus and a cell sorting method for the apparatus.

As apparatus for sorting cells, a fluorescent flow cytometer and a cell sorter are known. In these apparatus for sorting cells, the cells are kept on an air-liquid interface at a spout by surrounding fluid under proper vibration conditions generally including an exit flowing velocity of several m/s and a vibration frequency of several tens of kHz. At the same time, electric charge is also given to the cells. The cells each fly as a liquid drop in air, to which a static electric field is applied, in a direction according to the amount of the electric charge given thereto. Finally, the cells are sorted in a cell sorting container provided outside the flow channel.

For relatively high flowing velocities such as the one cited above, this technology is useful. In a flow cytometer with relatively low flowing velocities or a dielectric cytometer, however, it is difficult to satisfy a liquid-drop conversion condition and a discharging condition. Thus, it is desirable to rather provide a configuration in which a sorting operation is carried out on cells in a flow channel including branch flow channels and, at a later stage, the cells are held.

As a cell sorting mechanism in a flow channel, there has been proposed a method in accordance with which, for example, a piezo device or the like is used for changing the flowing direction of fluid in order to indirectly driving cells included in the fluid. However, the responsiveness of this mechanical device has a value in the order of about several milliseconds. Thus, if the responsiveness of a pressure wave in the flow channel is taken into consideration, this cell sorting mechanism provides a limited cell sorting speed.

As a method for directly driving cells, on the other hand, there has been proposed a dielectrophoretic-force method. A typical document such as JP-T-2003-507739 (refer to, among others, FIGS. 1 and 2) (hereinafter referred to as Patent Document 1) discloses the dielectrophoretic-force method in accordance with which a difference in dielectrophoretic force between cells flowing through a flow channel provided with embedded electrodes and a difference in sinking velocity between the cells are used to sort the cells into a plurality of cell groups having cell types different from each other.

SUMMARY

In comparison with, among others, a dielectrophoretic force applied to a cell, however, a difference in dielectrophoretic force between cell types is extremely small. In addition, the cell diameter, the cell cycle length and the like vary from cell to cell among cells virtually having the same cell type. If the small difference in dielectrophoretic force between cells and the variations of the cell diameter, the cell cycle length and the like are taken into consideration, it is expected that such a cell sorting method will not actually work well.

It is thus desirable to provide, for example, a cell sorting apparatus capable of sorting cells with a high degree of responsiveness and with absolute certainty even in an environment of a low flowing velocity. In addition, it is also desirable to provide, for example, a cell sorting chip for constructing the cell sorting apparatus and a cell sorting method to be adopted by the cell sorting apparatus.

A cell sorting apparatus according to an example embodiment of the present disclosure has a flow channel, an electric-field application section and a flow splitting section. The flow channel is a channel through which fluid including cells flows.

The electric-field application section is capable of applying an electric field having a gradient in a direction different from the flowing direction of the fluid at a first position on the flow channel in accordance with a cell sorting signal requesting an operation to sort the cells.

The flow splitting section is a section for splitting the cells changing their flowing directions due to a dielectrophoretic force caused by application of the electric field at a second position on the downstream side of the first position on the flow channel.

The present disclosure focuses attention on the fact that the gradient of the electric field is extremely large in comparison with, among other methods, the cell sorting method relying on a difference in dielectrophoretic force between cell types of cells each experiencing a dielectrophoretic force. In addition, in accordance with a cell sorting signal generated preliminarily by sections ranging from a measurement section to a measured-value analysis section by adoption of some techniques, the electric-field application section turns the electric field on and off or modulates the amplitude of the electric field and selectively applies the electric field to the cells in order to give a dielectrophoretic force to each of the cells. Thus, even in the case of a cell group in which the cell diameter and the cell physicality vary from cell to cell, by applying a sufficiently large dielectrophoretic force to only each of the cells used as the subject of sorting, for example, the cells can be sorted with a high degree of responsiveness and with absolute certainty even in an environment of a low flowing velocity.

In addition, it is also possible to provide an example embodiment of the present disclosure with a configuration in which the electric-field application section has a plurality of electrode pairs for creating the electric field and control of the electric field is carried out individually on each of the electrode pairs or each of electrode-pair groups obtained by grouping the electrode pairs.

In an example embodiment of the present disclosure, the electrode pairs each for creating an electric field for generating a dielectrophoretic force are provided typically on the flow channel and the electrode pairs are divided into a plurality of electrode-pair groups cited above. Then, control of the electric field is carried out individually on each of the electrode pairs or each of the electrode-pair groups. Thus, by carrying out the control of the electric field, for example, each cell can be sorted selectively with absolute certainty even if a plurality of cells exist in a cell sorting area including the electrode pairs.

In addition, it is also possible to provide an example embodiment of the present disclosure with a configuration in which the electric-field application section has a plurality of electrode pairs for creating the electric field and the electrode pairs are provided in such a way that locations at which maximum dielectrophoretic forces are generated by the electrode pairs are aligned along an average locus of cells with flowing directions thereof changed by the dielectrophoretic forces.

By providing electrode pairs in accordance with an example embodiment of the present disclosure as described above, it is possible to effectively make use of the location dependence of the dielectrophoretic force. Thus, the number of electrode pairs and, hence, the cost can be reduced.

In addition, it is also possible to provide an example embodiment of the present disclosure with a configuration in which, in order to create the electric field having a gradient, the electric-field application section is provided with an electrode pair having a signal application electrode for receiving a signal as well as a common electrode and, in an area other than an area for creating the electric field having a gradient, a gap between the signal application electrode and the common electrode is fixed.

In an example embodiment of the present disclosure, at a certain portion between two electric pairs separated away from each other in a main flowing direction serving as the flowing direction of fluid including cells, there is undesirably a location at which a dielectrophoretic force is generated in a reverse direction against the movement of the cells. By making use of a common electrode, however, when a cell is migrating in the main flowing direction, there is no portion in which the reverse-direction dielectrophoretic force works or the magnitude of the reverse-direction dielectrophoretic force is so small in comparison with an area of a normal-direction dielectrophoretic force so that the reverse-direction dielectrophoretic force may be ignored.

A cell sorting chip according to an example embodiment of the present disclosure has a substrate, an input section, a flow channel, a pair of electrodes, and a flow splitting section.

The flow channel is provided on the substrate. The flow channel is a channel through which liquid including cells flows.

The input section is also provided on the substrate. The input section receives a cell sorting signal for sorting the cells.

The pair of electrodes is provided at a first position on the flow channel. The pair of electrodes applies an electric field having a gradient in a direction different from the flowing direction of the fluid on the basis of the cell sorting signal received from the input section.

The flow splitting section is a section for splitting the cells changing their flowing directions due to a dielectrophoretic force caused by application of the electric field at a second position on the downstream side of the first position on the flow channel.

Thus, in an example embodiment of the present disclosure, by making use of the cell sorting chip having the configuration described above, even in the case of a cell group in which the cell diameter and the cell physicality vary from cell to cell, by applying a sufficiently large dielectrophoretic force to only each of cells used as the subject of sorting, for example, the cells can be sorted with a high degree of responsiveness and with absolute certainty even in an environment of a low flowing velocity.

In accordance with a cell sorting method according to an example embodiment of the present disclosure, fluid including cells is driven to flow through a flow channel. Then, an electric field having a gradient in a direction different from the flowing direction of the fluid is selectively applied at a first position on the flow channel on the basis of a cell sorting signal. Subsequently, the cells changing their flowing directions due to a dielectrophoretic force caused by application of the electric field at a second position on the downstream side of the first position on the flow channel are split in a cell sorting operation.

Thus, in an example embodiment of the present disclosure, by adoption of the cell sorting method described above, even in the case of a cell group in which the cell diameter and the cell physicality vary from cell to cell, by applying a sufficiently large dielectrophoretic force to only each of cells used as the subject of sorting, for example, the cells can be sorted with a high degree of responsiveness and with absolute certainty even in an environment of a low flowing velocity.

In accordance with the present disclosure, cells may be sorted with a high degree of responsiveness and with absolute certainty even in an environment of a low flowing velocity.

Additional features and advantages are described herein, and will be apparent from the following Detailed Description and the figures.

BRIEF DESCRIPTION OF THE FIGURES

FIG. 5 is a diagram showing a top view of a configuration of the electric-field application section of the cell sorting section employed in the cell sorting chip shown in FIG. 2 with the cell sorting signal turned on.

DETAILED DESCRIPTION

Embodiments of the present application will be described below in detail with reference to the drawings.

A Cell-Function Analyzing/Sorting System

Figure 1:
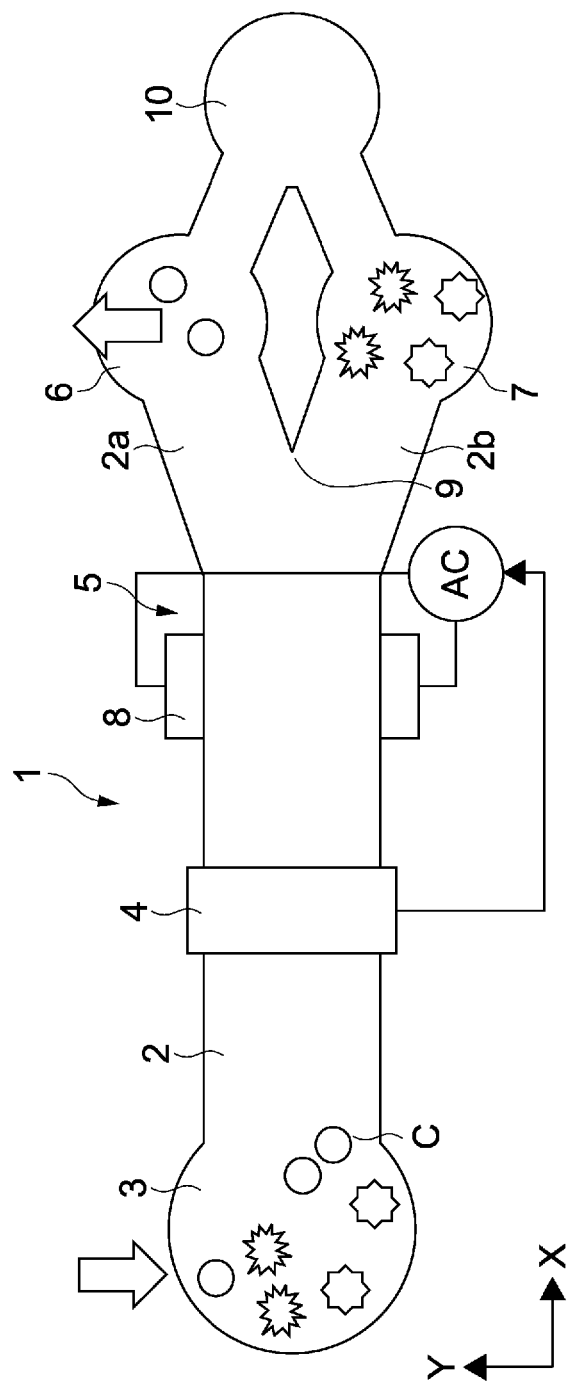
FIG. 1 is a conceptual diagram showing a cell-function analyzing/sorting system according to an example embodiment of the present disclosure.

FIG. 1 is a conceptual diagram showing a cell-function analyzing/sorting system 1 according to an example embodiment of the present disclosure.

As shown in FIG. 1, the cell-function analyzing/sorting system 1 has an injection section 3, a measurement section 4, a cell sorting section 5, cell fetching sections 6 and 7 as well as an outflow section 10 which are arranged along a micro flow channel 2 referred to hereafter simply as a flow channel 2.

The injection section 3 is a section for receiving liquid injected into the injection section 3 by making use of typically a pump as liquid including sampled cells C.

The flow channel 2 is a channel through which the liquid injected into the injection section 3 flows.

The measurement section 4 is a section for measuring the complex dielectric constant of a cell C at frequency points in a frequency range of typically 0.1 MHz to 50 MHz for each individual cell C flowing through the flow channel 2. The frequency range is a range in which the dielectric relaxation phenomenon of a cell C occurs. The measurement section 4 measures the complex dielectric constant of a cell C at typically three or more frequency points. For example, the measurement section 4 measures the complex dielectric constant of a cell C at 10 to 20 frequency points. On the basis of the measured complex dielectric constants of a cell C, the measurement section 4 determines whether or not the cell C is a cell to be sorted. If the cell C is a cell to be sorted, the measurement section 4 outputs a cell sorting signal. The measurement section 4 can be configured to typically include a signal detection section and a cell-function analyzing section. The signal detection section is configured to typically include a pair of electrodes whereas the cell-function analyzing section is a section for analyzing the function of the cell C on the basis of the detected signal.

The cell sorting section 5 selects a desired cell C from a plurality of cells C injected by the injection section 3 as cells C of different types and supplies the desired cell C to the cell fetching section 6 and the other cells C to the cell fetching section 7 in the so-called cell sorting process. The cell sorting section 5 has an electric-field application section 8 and a flow splitting section 9.

The electric-field application section 8 provided in the cell sorting section 5 is a section capable of applying an electric field having a gradient in a direction different from the X direction in which the fluid flows. For example, the electric-field application section 8 is capable of applying an electric field having a gradient in a Y direction perpendicular to the X direction which is the flowing direction of the fluid. Typically, when the cell sorting signal serving is not received, the electric-field application section 8 does not apply an electric field. When the cell sorting signal is received, on the other hand, the electric-field application section 8 applies an electric field. Of course, it is possible to provide a configuration in which, conversely, when the cell sorting signal is received, the electric-field application section 8 does not apply an electric field but, when the cell sorting signal is not received, on the other hand, the electric-field application section 8 applies an electric field.

The flow splitting section 9 employed in the cell sorting section 5 is a section for directing a cell C to which the electric-field application section 8 does not apply the electric field to the cell fetching section 7 through a branch flow channel 2b and a cell C experiencing the electric field generated by the electric-field application section 8 to the cell fetching section 6 through a branch flow channel 2a.

The cell fetching sections 6 and 7 are connected to the outflow section 10 through the flow channel 2. The fluid passing through the cell fetching sections 6 and 7 is exhausted by a pump from the outflow section 10 to an external destination.

If an electric field is applied to a cell C existing in the fluid serving as a flowing medium, due to a difference in polarizability between the flowing medium and the cell C, an induced dipole moment is generated. If the electric field is not uniform, the strength of the electric field varies in the surroundings of the cell C so that an induced dipole moment generates a dielectrophoretic force expressed by Eq. (1) given below. In Eq. (1), notation $\in'm$ denotes the real part of the complex specific dielectric constant, notation $\in v$ denotes the vacuum dielectric constant, notation R denotes the radius of the cell C and notation $E_{rms}$ denotes the RMS value of the applied electric field. The complex specific dielectric constant is defined by Eq. (2) also given below. In addition, notation K used in Eq. (1) is the Clausius-Mossotti function expressed by Eq. (3) also given below. In Eq. (3), notations $\in^*p$ and $\in^*m$ denote the coefficient constants of the cell C and the flowing medium respectively.

$$\langle \overline{F}_{DEP}(t) \rangle = 2\pi \varepsilon'_m \varepsilon_v R^3 \text{Re}[K(\omega)] \nabla E^2_{rms} \quad (1)$$

$$\varepsilon^* = \varepsilon' - i\varepsilon'' + \frac{\kappa}{i\omega\varepsilon_v} \quad (2)$$

$$K(\omega) = \frac{\varepsilon^* p - \varepsilon^* m}{\varepsilon^* p + 2\varepsilon^* m} \quad (3)$$

As already explained before, in accordance with the method disclosed in Patent Document 1, attention is paid to the difference in K between cells C are sorted by adoption of a dielectrophoretic force technique alone. In the case of the cell-function analyzing/sorting system 1, on the other hand, the difference in dielectrophoretic force between call types does not daringly make use of the dependence on the frequency. Instead, in accordance with a cell sorting signal generated preliminarily by sections ranging from a measurement section to a measured-value analysis section by adoption of some techniques, the electric-field application section turns the electric field on and off or modulates the amplitude of the electric field and selectively applies the electric field to the cells C in order to give a dielectrophoretic force to each of the cells C. Thus, even in the case of a cell group in which the cell diameter and the cell physicality vary from cell to cell, by applying a sufficiently large dielectrophoretic force to only each of cells C used as the subject of sorting for example, the cells C can be sorted with a high degree of responsiveness and with absolute certainty.

Cell-Function Analyzing/Sorting Chip

Figure 2:
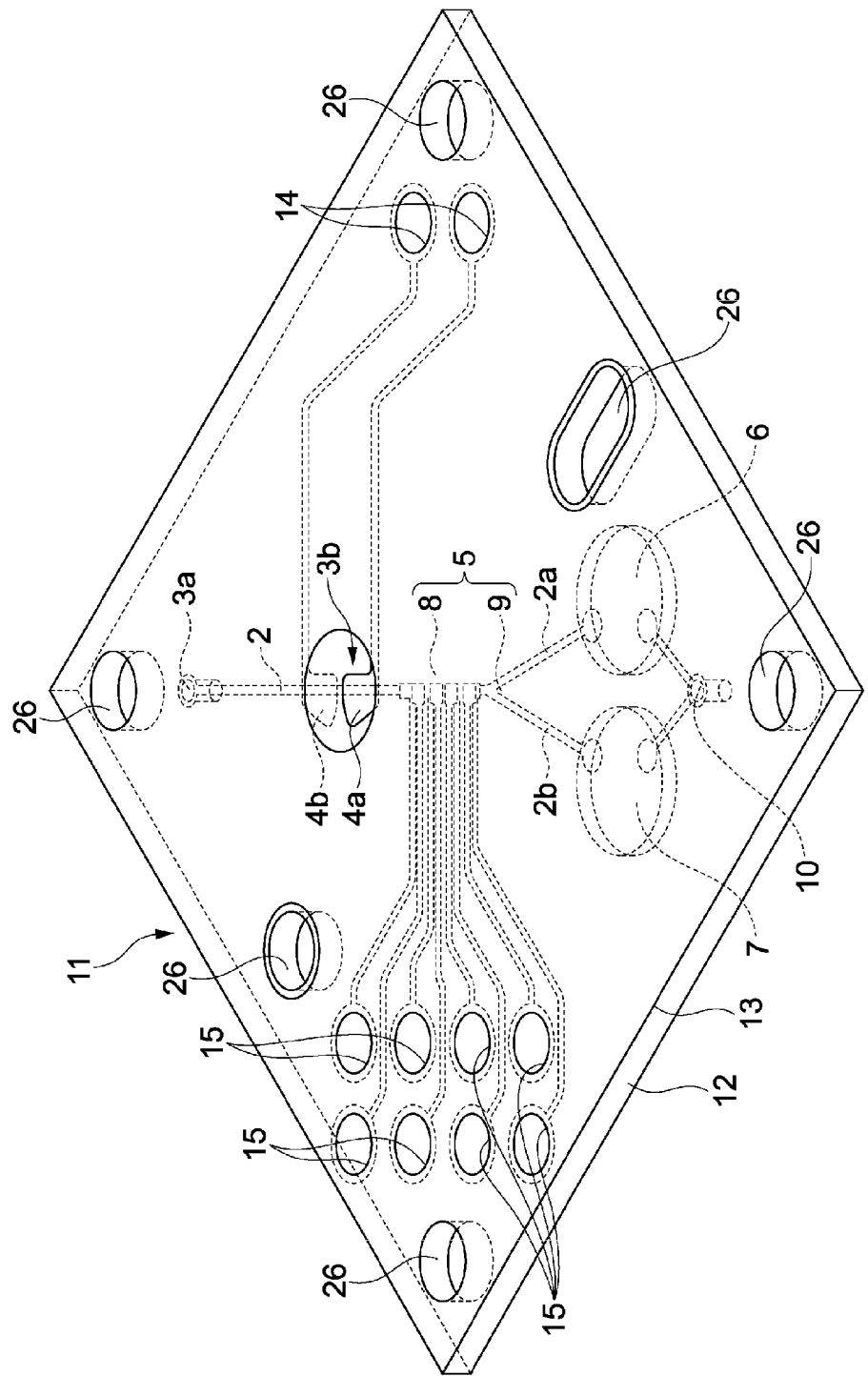
FIG. 2 is a perspective diagram showing a configuration of a cell sorting chip useable in the cell-function analyzing/sorting system shown in FIG. 1.

FIG. 2 is a perspective diagram showing an example configuration of a cell sorting chip 11 useable in the cell-function analyzing/sorting system 1 shown in FIG. 1.

As shown in FIG. 2, the cell sorting chip 11 has a substrate 12 and a member 13 made from a high-molecular film or the like to form the shape of a sheet. On the substrate 12, there are provided the flow channel 2, the branch flow channels 2a and 2b which are each a portion of the flow channel 2, a liquid injection section 3a functioning as the injection section 3, the flow splitting section 9 which is a portion of the flow channel 2, the cell fetching sections 6 and 7 as well as the outflow section 10. The flow channel 2, the branch flow channels 2a and 2b, the liquid injection section 3a, the flow splitting section 9, the cell fetching sections 6 and 7 as well as the outflow section 10 are constructed into a configuration provided on the substrate 12 by creating grooves or the like on the surface of the substrate 12 and by covering the surface with the sheet-shaped member 13. In this way, the flow channel 2 is created.

A cell injection section 3b into which the fluid including cells C is injected is configured by providing a tiny hole on the sheet-shaped member 13 to serve as a stenosis channel. When the fluid including cells C is dropped on the cell injection section 3b by making use of a pipette, the fluid flows through the flow channel 2 to the downstream side of the flow channel 2 so that the fluid is mixed up with liquid flowing along the flow channel 2 through the stenosis channel. Since the stenosis channel is a tiny hole, cells C never flow through the stenosis channel to the flow channel 2 as a group. Instead, only a single cell C is capable of passing through the stenosis channel sequentially one cell after another to the flow channel 2.

A pair of measurement electrodes 4a and 4b for measuring a complex resistance or a complex dielectric constant is provided to sandwich the stenosis channel. The pair of measurement electrodes 4a and 4b is provided to serve as a first electrode pair. The measurement electrode 4a which is a specific one of the electrodes is provided on the front face of the sheet-shaped member 13 whereas the measurement electrode 4b serving as the other electrode is provided on the rear face of the sheet-shaped member 13. An electrode pair composing the electric-field application section 8 is also provided on the rear face of the sheet-shaped member 13. This electrode pair will be described later.

The cell fetching sections 6 and 7 are covered by the sheet-shaped member 13 provided above the cell fetching sections 6 and 7. However, a cell C can be fetched through a pipette by stinging the sheet-shaped member 13 with the pipette.

An electrode pad 14 is a section for fetching a signal detected by the measurement electrodes 4a and 4b and outputting the fetched signal to an external signal recipient. The fetched signal is typically transmitted to a cell-function analyzing section not shown in the figure.

An electrode pad 15 serves as an input section for receiving a cell sorting signal from the cell-function analyzing section. The received cell sorting signal is transmitted to the electrode pair composing the electric-field application section 8 as described above.

A through hole 26 is a hole which is used for determining a position at which the cell sorting chip 11 is mounted on the main body having the cell-function analyzing section.

Configuration of the Cell Sorting Section

Figure 3:
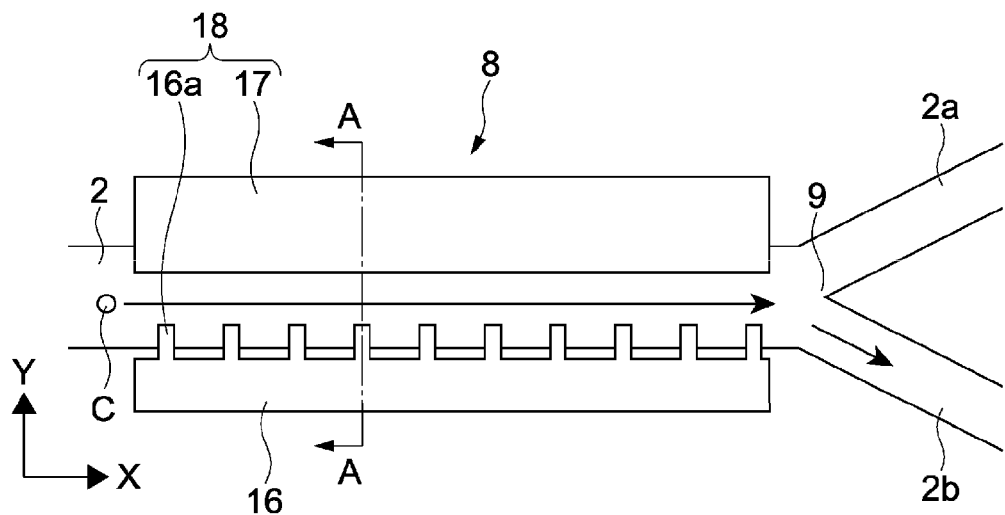
FIG. 3 is a diagram showing a top view of a configuration of an electric-field application section of a cell sorting section employed in the cell sorting chip shown in FIG. 2 with a cell sorting signal turned off.
Figure 4:
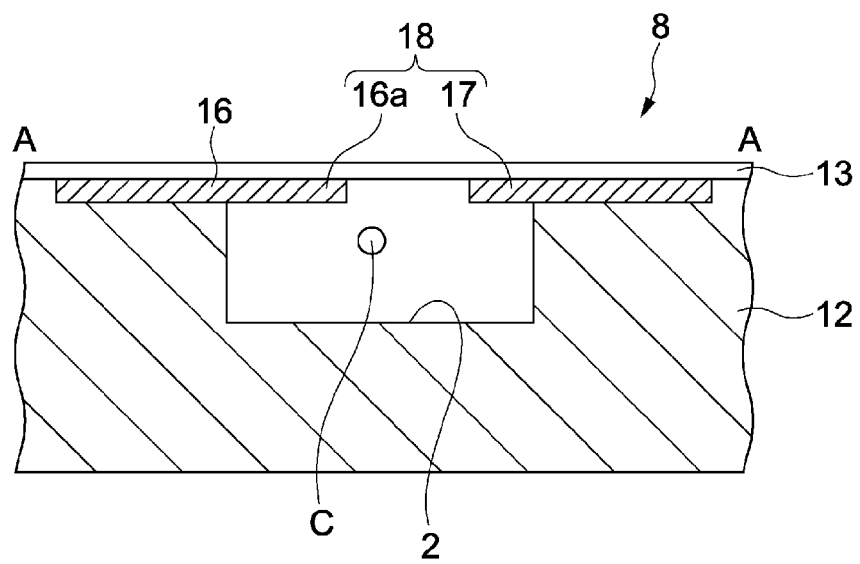
FIG. 4 is a diagram showing a cross section along a line A-A shown in FIG. 3.

FIG. 3 is a diagram showing a top view of an example configuration of an electric-field application section 8 of a cell sorting section 5 employed in the cell sorting chip 11 shown in FIG. 2 with a cell sorting signal turned off whereas FIG. 4 is a diagram showing a cross section along a line A-A shown in FIG. 3.

As shown in FIGS. 3 and 4, the cell sorting section 5 has the electric-field application section 8 and the flow splitting section 9.

The electric-field application section 8 has electrodes 16 and 17 provided at predetermined positions on the flow channel 2. For example, the electrodes 16 and 17 are provided at predetermined positions which sandwich the flow channel 2 and face each other in a Y direction different from the X flowing direction of the fluid flowing through the flow channel 2.

The electrodes 16 and 17 are provided on the rear face of the member 13 having a sheet shape. The rear face of the sheet-shaped member 13 is a ceiling face inside the flow channel 2. The electrode 16 is typically an electrode to which a signal is applied. The electrode 16 is configured to have a number of electrode pointers 16a each protruding in a direction toward the electrode 17. The electrode 17 is typically the common electrode. The electrode 17 is configured to have neither protrusions nor dents in a direction in which the electrode 17 faces the electrode 16. In the following description, a combination of one electrode pointer 16a and the electrode 17 is referred to as an operation-electrode pair 18.

With the operation-electrode pair 18 configured as described above, when a signal is applied to the electrodes 16 and 17, an electric field having a gradient in the Y direction is applied to each operation-electrode pair 18.

Placed at a predetermined position on the downstream side of the electric-field application section 8 on the flow channel 2, the flow splitting section 9 is a section for changing the flowing direction of a cell C by making use of a dielectrophoretic force caused an electric field applied by the electric-field application section 8. The flow splitting section 9 is configured to have the shape of the Y character for splitting the fluid flowing through the flow channel 2 into fluid flowing to the cell fetching section 6 through the branch flow channel 2a and fluid flowing to the cell fetching section 7 through the branch flow channel 2b.

For example, at the injection section 3, a cell C is injected to a position sided to the cell fetching section 7. This cell C injected to a position sided to the cell fetching section 7 is put in a non-active state and flows inside the flow channel 2 to the cell fetching section 7 through the position sided to the cell fetching section 7 by sustaining its flowing direction as it is and through the flow splitting section 9 to enter the branch flow channel 2b connected to the cell fetching section 7 as shown in FIG. 3. An active state is a state in which a cell C not serving as the subject of cell sorting does not experience an electric field at the electric-field application section 8 when the cell C is passing through the electric-field application section 8.

Figure 5:
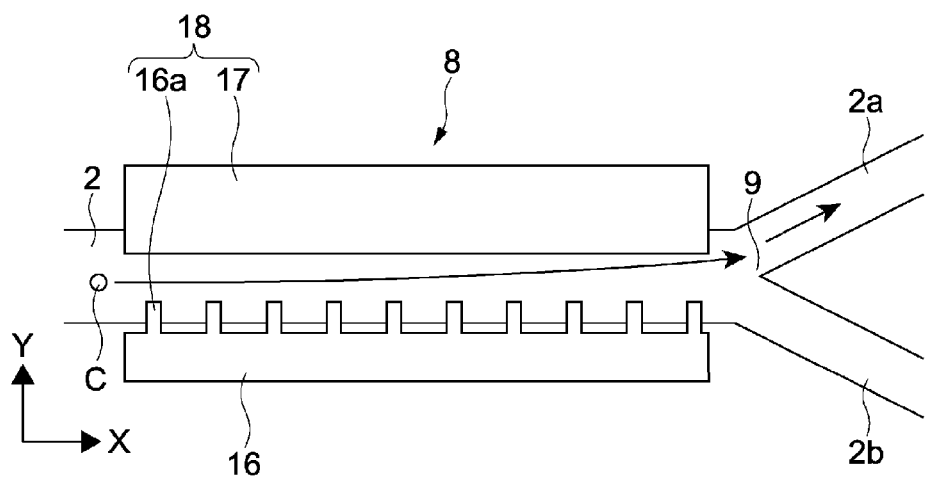

If the cell C injected to a position sided to the cell fetching section 7 is put in an active state, however, the cell C flows inside the flow channel 2 through the position sided to the cell fetching section 7 by changing its flowing direction to the cell fetching section 6 and through the flow splitting section 9 to enter the branch flow channel 2a connected to the cell fetching section 6 as shown in FIG. 5. A non-active state is a state in which a cell C serving as the subject of cell sorting experiences a dielectrophoretic force generated by an electric field applied by the electric-field application section 8 when the cell C is passing through the electric-field application section 8.

In the electric-field application section 8 configured as described above, each operation-electrode pair 18 applies an electric field having a gradient in the Y direction. Thus, a cell C passing through the electric-field application section 8 gradually changes its flow channel and branches to the side of the cell fetching section 6 by flowing through the branch flow channel 2a.

First Other Example Configuration of the Electric-Field Application Section

The dielectrophoretic force applied to a cell C in an electric field having a strength not causing a fatal damage to the cell C has a value of the order of several mm/s. Thus, it is necessary to provide a number of non-uniform electric fields each used for deliberately generating a dielectrophoretic force in a direction perpendicular to the flowing direction or a number of electrode-pair columns each consisting of operation-electrode pairs 18 each used for generating such an electric field. As shown in FIGS. 3 and 5, if a voltage is applied to the numerous operation-electrode pairs 18 at the same time, an electrode column sorting area of the operation-electrode pairs 18 must be used exclusively so that the throughput does not increase in some cases.

Figure 6:
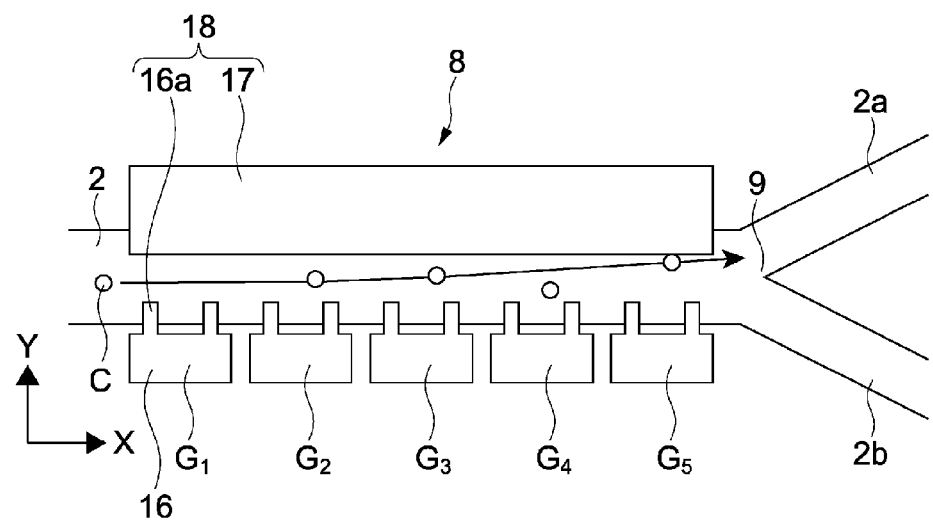
FIG. 6 is a diagram showing a top view of a first other example configuration of the electric-field application section of the cell sorting section.

In order to solve the problem described above, the operation-electrode pairs 18 are divided into a plurality of electrode-pair groups such as electrode-pair groups G1 to G5 arranged in the X direction as shown in FIG. 6 and a voltage applied individually to each of the electrode-pair groups G1 to G5 is controlled in order to allow multiplexing of cells C passing through the electric-field application section 8. In this way, the throughput can be increased. That is to say, in the case of the electric-field application section 8 having a configuration shown in FIGS. 3 and 5, it is necessary to let a cell C flow to the flow channel 2 with such a timing that, until a specific cell C passes through the electric-field application section 8, a cell C coming after the specific cell C is prevented from flowing to the flow channel 2. In the case of the electric-field application section 8 having a configuration shown in FIG. 6, on the other hand, it is possible to carry out control to apply an electric field to, for example, a cell C currently passing through the electrode-pair group G5 but apply no electric field to a cell C currently passing through the electrode-pair group G4. As a result, it is possible to carry out sorting control on cells C in each of the five electrode-pair groups G1 to G5.

Figure 7:
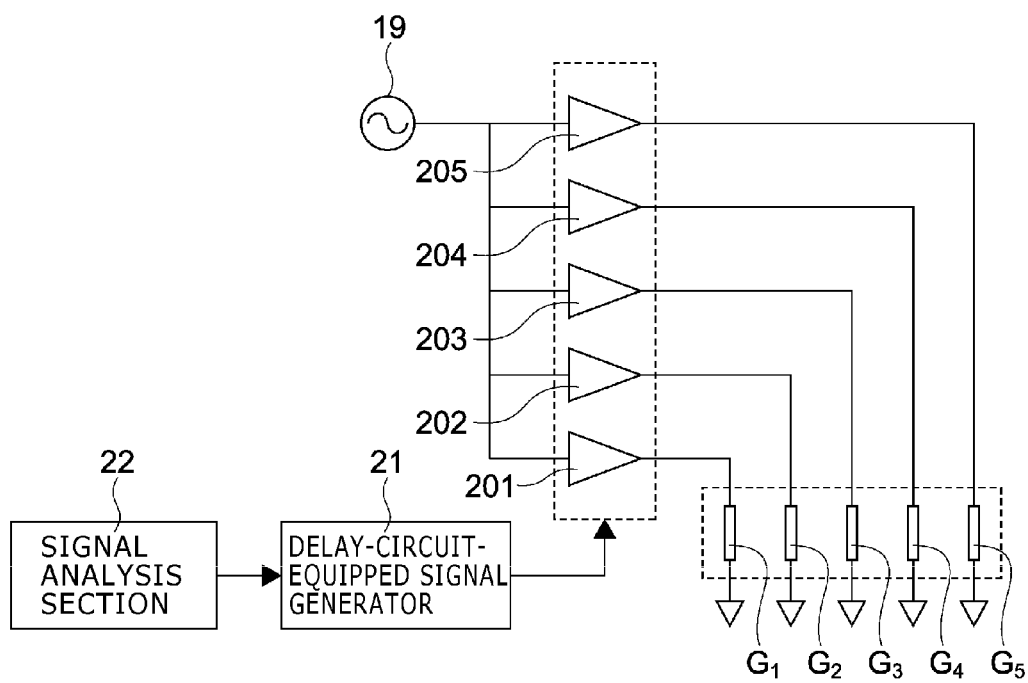
FIG. 7 is a block diagram showing a configuration for controlling application of an electric field to each group of electrode pairs in the electric-field application section shown in FIG. 6.

FIG. 7 is a block diagram showing a configuration for controlling application of an electric field to each group of electrode pairs in the electric-field application section 8 shown in FIG. 6.

Figure 8:
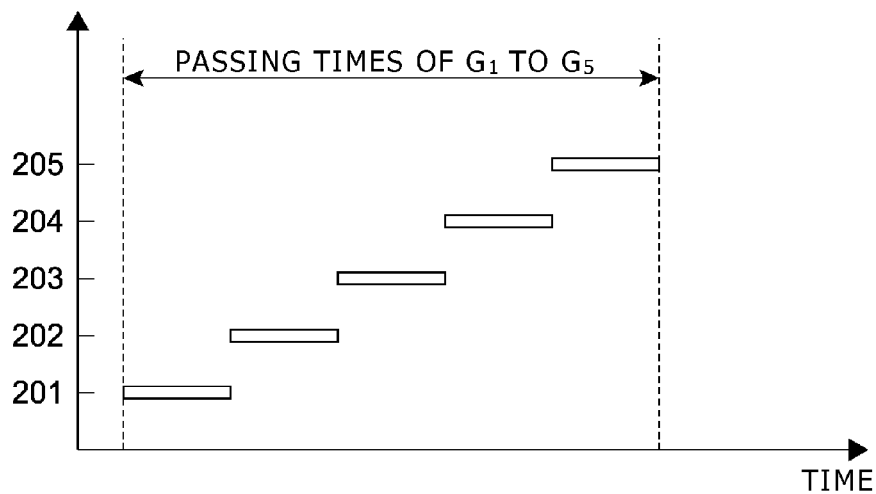
FIG. 8 is a diagram showing example timings of an enable signal supplied to each amplifier employed in the configuration shown in FIG. 7.

As shown in FIG. 7, a signal generated by an AC source 19 for applying an electric field is amplified by amplifiers 201 to 205 and the five amplified signals are supplied to the electrode-pair groups G1 to G5 respectively. When a delay-circuit-equipped signal generator 21 receives a cell sorting signal from a signal analysis section 22, as shown in FIG. 8, enable signals are supplied sequentially to the amplifiers 201, 202, 203, 204 and 205 in their enumeration order. The periods in which the enable signals are supplied sequentially to the amplifiers 201, 202, 203, 204 and 205 coincide with the periods in which the cell C to be sorted is passing through the electrode-pair groups G1, G2, G3, G4 and G5 respectively. Thus, if the cell C arriving in the area of the electric-field application section 8 is a cell C to be sorted, when the cell C to be sorted is passing through the electrode-pair groups G1, G2, G3, G4 and G5 in their enumeration order, the enable signals are supplied sequentially to the amplifiers 201, 202, 203, 204 and 205 respectively in their enumeration order so that the flowing direction of the cell C is gradually changing to cause the cell C to branch to the cell fetching section 6.

It is to be noted that, the control described above can of course be carried out in electrode-pair units in place of electrode-pair group units.

Second Other Example Configuration of the Electric-Field Application Section

Figure 9:
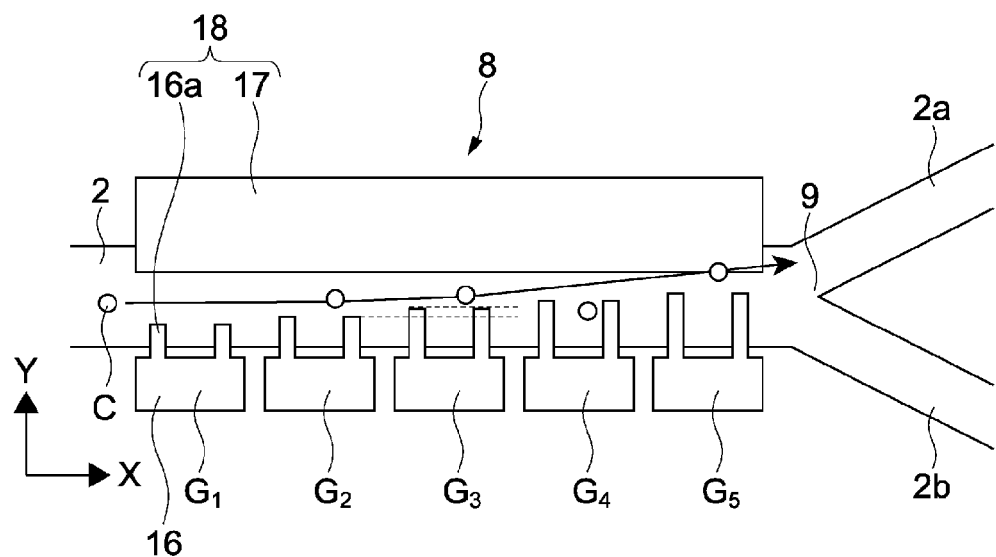
FIG. 9 is a diagram showing a top view of a second other example configuration of the electric-field application section employed in the cell sorting section.

FIG. 9 is a diagram showing a top view of a second other example configuration of the electric-field application section 8 employed in the cell sorting section 5.

As shown in FIG. 9, the electric-field application section 8 has a plurality of electrode pairs 18 for creating an electric field and the electrode pairs 18 are provided in such a way that locations at which maximum dielectrophoretic forces are generated by the electrode pairs 18 are aligned along an average locus of cells C with flowing directions thereof changed by the dielectrophoretic forces. In an electrode pair 18, the location at which the maximum dielectrophoretic force is generated is the tip 16b of an electrode pointer 16a included in the electrode pair 18. Thus, the electrode pairs 18 are provided in such a way that the tips 16b are aligned along an average locus of cells C with flowing directions thereof changed by the dielectrophoretic forces.

A column of electrode pairs 18 according to the present disclosure has been designed so that a non-uniform electric field effective for sorting a desired cell C is created. Due to the non-uniformity of the electric field, however, in a gap existing between a electrode pointer 16a and the common electrode 17 to serve as the gap in the electrode pair 18 composed of the electrode pointer 16a and the common electrode 17, the dependence of the dielectrophoretic force on the position exists. That is to say, in the gap between an electrode pointer 16a and the common electrode 17, the dielectrophoretic force is not constant. Instead, on the tip 16b of the electrode pointer 16a, the dielectrophoretic force is maximized. In the electric-field application section 8 shown in FIG. 9, the dependence of the dielectrophoretic force on the position is effectively used in order to reduce the number of electrode pairs 18 and, hence, the cost.

Third Other Example Configuration of the Electric-Field Application Section

Figure 10:
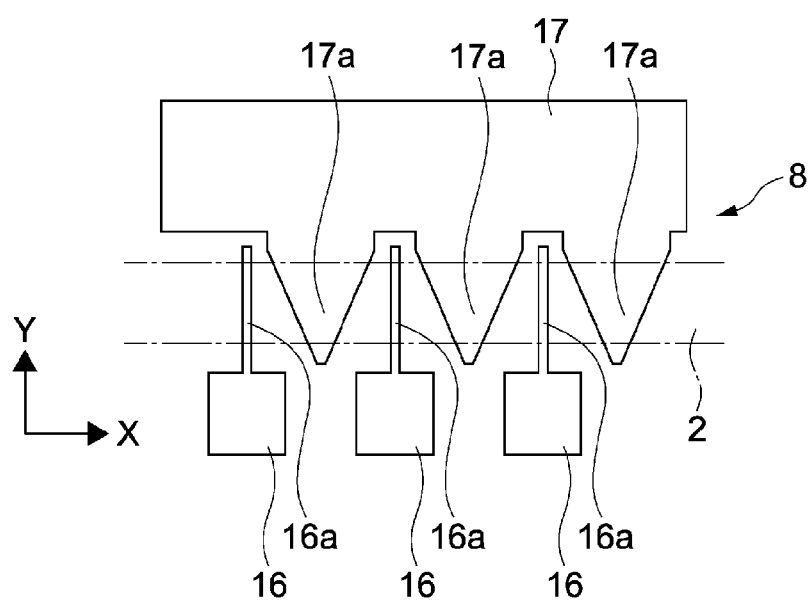
FIG. 10 is a diagram showing a top view of a third other example configuration of the electric-field application section employed in the cell sorting section.

FIG. 10 is a diagram showing a top view of a third other example configuration of the electric-field application section 8 employed in the cell sorting section 5.

As shown in FIG. 10, the electrode pointers 16a of the electrodes 16 in the electric-field application section 8 are provided at equal intervals to cross the flow channel 2 whereas the electrode pointers 17a of the common electrode 17 in the electric-field application section 8 are provided at equal intervals at positions between the adjacent electrode pointers 16a alternately with the adjacent electrode pointers 16a also to cross the flow channel 2. The electrode pointer 16a of each electrode 16 has the shape of a rectangle with two mutually facing sides thereof oriented in a direction perpendicular to the flowing direction of the liquid flowing through the flow channel 2. On the other hand, each of the electrode pointers 17a of the common electrode 17 has the shape of an isosceles triangle with the two equal sides thereof oriented in directions oblique to the adjacent electrode pointers 16a of the adjacent electrodes 16. On the common electrode 17, any two adjacent electrode pointers 17a on both sides of the electrode pointer 16a of every electrode 16 are symmetrical with respect to the electrode pointer 16a sandwiched by the electrode pointers 17a.

In the electric-field application section 8 configured as described above, the gradient of an electric field in the gap between two adjacent electrodes 16 or between two adjacent electrode pointers 17a of the common electrode 17 is uniform so that, when an electric field is being applied, a cell C serving as a subject of sorting is moving in an upward direction perpendicular to the page at a velocity proportional to the electric-field gradient raised to the second power.

Fourth Other Example Configuration of the Electric-Field Application Section

Figure 11:
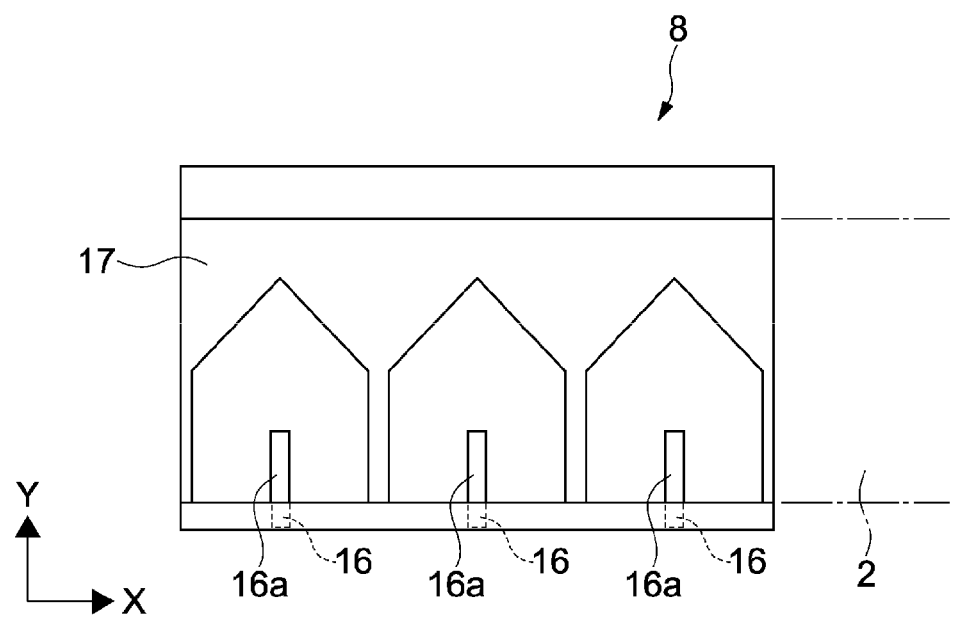
FIG. 11 is a diagram showing a top view of a fourth other example configuration of the electric-field application section employed in the cell sorting section.

FIG. 11 is a diagram showing a top view of a fourth other example configuration of the electric-field application section 8 employed in the cell sorting section 5.

As shown in FIG. 11, in the electric-field application section 8, the electrode pointer 16a of each electrode 16 protrudes against the flow channel 2, whereas the common electrode 17 encloses the electrode pointers 16a. Unlike the structures of the electrodes shown in FIG. 10, in the electric-field application section 8, in an area other than an area in which the electrode pointer 16a creates an electric field having a gradient, the gap between the electrode pointer 16a and the common electrode 17 is fixed. That is to say, in this other area, at a portion adjacent to an electrode pointer 16a, the common electrode 17 is parallel to the electrode pointer 16a. Thus, when a cell C is flowing in the main-flowing direction, there is not an interval in which a dielectrophoretic force is applied in the opposite direction or, even if such an interval exists, the dielectrophoretic force applied in the opposite direction has such a small magnitude that the dielectrophoretic force can be ignored.

Fifth Other Example Configuration of the Electric-Field Application Section

Figure 12:
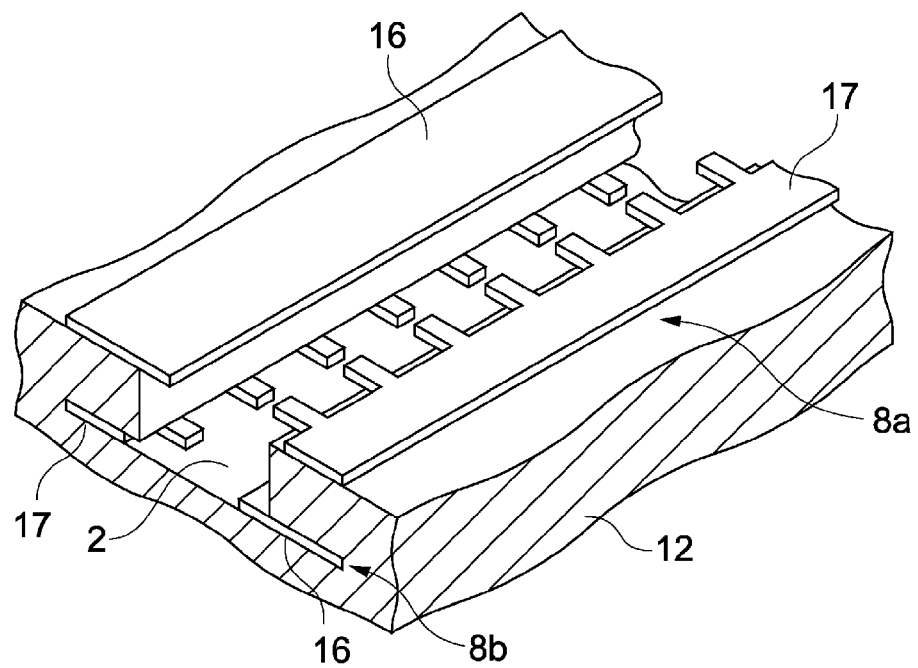
FIG. 12 is a perspective diagram showing a fifth other example configuration of the electric-field application section employed in the cell sorting section.

FIG. 12 is a perspective diagram showing a fifth other example configuration of the electric-field application section 8 employed in the cell sorting section 5.

As shown in FIG. 12, in the configuration of the electric-field application section 8, the electric-field application section 8 shown in FIG. 3 is provided at two locations on the floor and ceiling faces of the flow channel 2. The electric-field application section 8 provided on the ceiling face is denoted by reference numeral 8a whereas the electric-field application section 8 provided on the floor face is denoted by reference numeral 8b. The ceiling-side electric-field application section 8a applies a dielectrophoretic force to a cell C flowing through the flow channel 2 in a direction opposite to the direction of a dielectrophoretic force applied by the floor-side electric-field application section 8b to a cell C so that the cell C experiencing the dielectrophoretic force applied by the ceiling-side electric-field application section 8a is directed to the cell fetching section 6 whereas the cell C experiencing the dielectrophoretic force applied by the floor-side electric-field application section 8b is directed to the cell fetching section 7.

By configuring the electric-field application section 8 as described above, it is not necessary to inject a cell C into the injection section 3 at a position sided to the cell fetching section 6 or the cell fetching section 7. In addition, the cell C can be sorted with a higher degree of certainty.

Effects

Although it is necessary to provide some other means for preliminarily generating a cell sorting signal, even in the case of a cell group in which the cell diameter and the cell physicality vary from cell to cell, by applying a sufficiently large dielectrophoretic force to only each of cells C used as the subject of sorting for example, the cells can be sorted. Thus, in comparison with a cell sorting method for sorting cells C by relying on a difference in dielectrophoretic force sensitivity, it is possible to improve the cell sorting precision and the reliability which is absolutely required in cell medical cares and the like.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A cell sorting apparatus comprising:
   a flow channel including a first end and a second end opposite to the first end;
   an electric-field application section configured to provide an electric field on the flow channel;
   a flow splitting section including a plurality of channel branches connected to the second end of the flow channel; and
   a signal analysis section that includes a measurement electrode, wherein the signal analysis section is configured to provide a sorting signal for sorting cells,
   wherein the electric-field application section includes a plurality of electrode pairs, and the electric field is provided by each of the plurality of the electrode pairs or by each of electrode-pair groups in response to signals supplied to the plurality of electrode pairs or the electrode-pair groups, which each include at least two of the plurality of electrode pairs.

2. The cell sorting apparatus according to claim 1, wherein at least one of the plurality of electrode pairs includes a first electrode and a second electrode, and the first electrode includes a first electrode pointer protruding in a direction toward the second electrode.

3. The cell sorting apparatus according to claim 2, wherein a first gap exists between the first electrode pointer and the second electrode, and the first gap is adjacent to the first end of the flow channel, wherein a second gap exists between a second electrode pointer and the second electrode, and the second gap is adjacent to the second end of the flow channel, and wherein the second gap is smaller than the first gap.

4. The cell sorting apparatus according to claim 2, wherein a first gap exists between the first electrode pointer and the second electrode, and the first gap is adjacent to the first end of the flow channel, and a second gap exists between a second electrode pointer and the second electrode, and the second gap is adjacent to the second end of the flow channel, and wherein the second gap has a same gap distance as the first gap.

5. The cell sorting apparatus according to claim 2, wherein the first electrode is a signal application electrode and the second electrode is a common electrode.

6. The cell sorting apparatus according to claim 1, wherein the flow splitting section is a Y shape.

7. The cell sorting apparatus according to-claim 1, further comprising a signal generator that is configured to generate a sequence of enable signals in accordance with the sorting signal.

8. A cell sorting chip comprising:
   a substrate;
   a flow channel provided on the substrate and including a first end and a second end opposite to the first end; and
   an input connection provided on the substrate, the input connection configured to receive a cell sorting signal;
   an electric-field application section configured to provide an electric field on the flow channel; and
   a flow splitting section including a plurality of channel branches connected to the second end of the flow channel,
   wherein the electric-field application section includes a plurality of electrode pairs, and the electric field is provided by each of the plurality of the electrode pairs or by each of electrode-pair groups in response to signals supplied to the plurality of electrode pairs or the electrode-pair groups, which each include at least two of the plurality of electrode pairs.

9. The cell sorting chip according to claim 8, wherein at least one of the plurality of electrode pairs includes a first electrode and a second electrode, and the first electrode includes a first electrode pointer protruding in a direction toward the second electrode.

10. The cell sorting chip according to claim 9, wherein a first gap exists between the first electrode pointer and the second electrode, and the first gap is adjacent to the first end of the flow channel, wherein a second gap exists between a second electrode pointer and the second electrode, and the second gap is adjacent to the second end of the flow channel, and wherein the second gap is smaller than the first gap.

11. The cell sorting chip according to claim 9, wherein a first gap exists between the first electrode pointer and the second electrode, and the first gap is adjacent to the first end of the flow channel, wherein a second gap exists between a second electrode pointer and the second electrode, and the second gap is adjacent to the second end of the flow channel, and wherein the second gap has a same gap distance as the first gap.

12. The cell sorting apparatus according to claim 9, wherein the first electrode is a signal application electrode and the second electrode is a common electrode.

13. The cell sorting chip according to claim 8, wherein the flow splitting section is a Y shape.

14. The cell sorting chip according to claim 8, wherein the input connection includes an electrode pad.

15. A cell sorting method comprising:
   driving fluid including cells to flow through a flow channel;
   applying an electric field in a direction different from the flowing direction of the fluid in accordance with a cell sorting signal and a sequence of enable signals; and
   sorting the cells by changing their flowing directions due to the applied electric field,
   wherein the electric field is provided by each of a plurality of electrode pairs or each of electrode-pair groups in response to the enable signals supplied to the plurality of electrode pairs or the electrode-pair groups, which each include at least two of the plurality of electrode pairs.

16. The cell sorting method according to claim 15, wherein the electric field applied perpendicular to the flowing direction of the fluid.

17. The cell sorting apparatus according to claim 1, wherein the measurement electrode is configured to measure a complex resistance.

18. The cell sorting apparatus according to claim 1, wherein the measurement electrode is configured to measure a complex dielectric constant.

19. The cell sorting chip according to claim 8, further comprising a measurement electrode.

20. The cell sorting chip according to claim 19, wherein the measurement electrode is configured to measure at least one of a complex resistance and a complex dielectric constant.

* * * * *